(12) United States Patent
Newby

(10) Patent No.: US 9,572,930 B2
(45) Date of Patent: Feb. 21, 2017

(54) PASSIVELY SHIELDING NEEDLE ASSEMBLY WITH SKIN SENSOR

(75) Inventor: C. Mark Newby, Tuxedo, NY (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 906 days.

(21) Appl. No.: 13/810,311

(22) PCT Filed: Jul. 29, 2010

(86) PCT No.: PCT/US2010/043726
§ 371 (c)(1),
(2), (4) Date: Jul. 8, 2013

(87) PCT Pub. No.: WO2012/015415
PCT Pub. Date: Feb. 2, 2012

(65) Prior Publication Data
US 2013/0281972 A1   Oct. 24, 2013

(51) Int. Cl.
*A61M 5/162* (2006.01)
*A61B 5/15* (2006.01)
(Continued)

(52) U.S. Cl.
CPC ............ *A61M 5/1626* (2013.01); *A61B 5/153* (2013.01); *A61B 5/15003* (2013.01);
(Continued)

(58) Field of Classification Search
CPC .............. A61M 5/1626; A61M 2005/3107; A61M 5/32; A61M 5/3202; A61M 5/3204; A61M 5/321; A61M 5/322; A61M 5/3243; A61M 5/326; A61B 5/150633; A61B 5/150648; A61B 5/150679

See application file for complete search history.

(56) References Cited

U.S. PATENT DOCUMENTS 4,270,537 A * 6/1981 Romaine ................. A61M 5/46
                                                           604/117
5,059,180 A   10/1991 McLees
(Continued)

FOREIGN PATENT DOCUMENTS

EP   1369142 A1   12/2003
JP   2002521143 A   7/2002
(Continued)

*Primary Examiner* — Imani Hayman
*Assistant Examiner* — Nilay Shah
(74) *Attorney, Agent, or Firm* — The Webb Law Firm

(57) ABSTRACT

A shielding needle assembly is provided with a hub having a needle cannula with a puncture tip extending from a forward end thereof, and a shield member in telescoping association with the hub. A drive member biases the hub and the shield member away from each other for relative telescopic movement between a first position in which the puncture tip extends from a forward end of the shield member, and a second position in which the puncture tip is encompassed within the shield member. A pivoting lever maintains the hub and the shield member in the first position against the bias of the drive member with the needle cannula exposed for use. The lever is pivotable during contact with a patient's skin surface such as during venipuncture, thereby releasing the hub and the shield member from the first position and permitting the drive member to bias the hub and the shield member toward the second position.

20 Claims, 17 Drawing Sheets

(51) Int. Cl.
*A61B 5/153* (2006.01)
*A61M 5/158* (2006.01)
*A61M 5/32* (2006.01)
*A61M 5/31* (2006.01)

(52) U.S. Cl.
CPC .... *A61B 5/15074* (2013.01); *A61B 5/150259* (2013.01); *A61B 5/150389* (2013.01); *A61B 5/150519* (2013.01); *A61B 5/150648* (2013.01); *A61M 5/158* (2013.01); *A61M 5/321* (2013.01); *A61M 5/322* (2013.01); *A61M 5/3202* (2013.01); *A61M 5/326* (2013.01); *A61M 5/3243* (2013.01); *A61M 2005/3107* (2013.01)

(56) References Cited

U.S. PATENT DOCUMENTS

| | | |
|---|---|---|
| 5,104,384 A | 4/1992 | Parry |
| 5,125,414 A | 6/1992 | Dysarz |
| 6,228,054 B1 | 5/2001 | Dysarz |
| 6,537,259 B1 | 3/2003 | Niermann |
| 6,547,762 B1 * | 4/2003 | Botich .............. A61M 25/0631 604/110 |
| 6,682,510 B2 | 1/2004 | Niermann |
| 6,830,560 B1 | 12/2004 | Gross et al. |
| 6,832,992 B2 | 12/2004 | Wilkinson |
| 6,881,202 B2 | 4/2005 | Coleman et al. |
| 7,150,725 B2 | 12/2006 | Wilkinson |
| 7,201,740 B2 | 4/2007 | Crawford |
| 7,294,118 B2 | 11/2007 | Saulenas et al. |
| 7,357,783 B2 | 4/2008 | Millerd |
| 7,361,159 B2 | 4/2008 | Fiser et al. |
| 7,753,878 B2 | 7/2010 | Jones et al. |
| 2003/0078540 A1 | 4/2003 | Saulenas et al. |
| 2005/0119635 A1 | 6/2005 | Crawford |
| 2006/0195061 A1 * | 8/2006 | Besing ................ A61M 5/1785 604/110 |
| 2007/0066937 A1 * | 3/2007 | Jones ................... A61M 5/158 604/110 |
| 2007/0066960 A1 | 3/2007 | Jones et al. |
| 2008/0306452 A1 * | 12/2008 | Crawford .......... A61M 25/0631 604/263 |
| 2009/0259201 A1 | 10/2009 | Hwang et al. |
| 2009/0281492 A1 | 11/2009 | Millerd |

FOREIGN PATENT DOCUMENTS

| | | |
|---|---|---|
| JP | 2009509585 A | 3/2009 |
| WO | 0006221 A1 | 2/2000 |

* cited by examiner

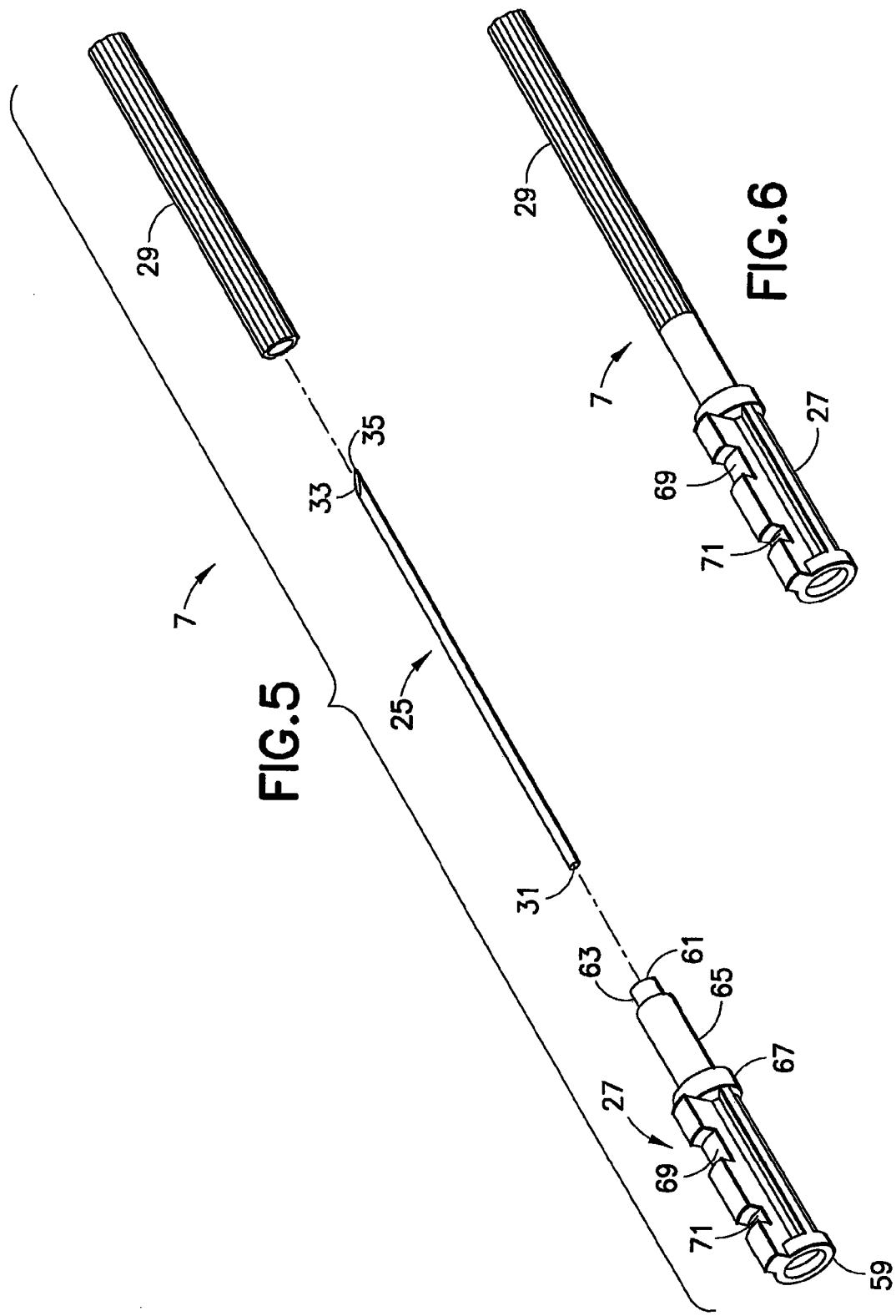

PASSIVELY SHIELDING NEEDLE ASSEMBLY WITH SKIN SENSOR

BACKGROUND OF THE INVENTION

Field of the Invention

The present invention relates to blood collection sets for safe and convenient handling of needles used in blood collection procedures. More particularly, the present invention relates to a blood collection set including a safety shield for protecting users from a used needle tip.

Description of Related Art

Disposable medical devices having medical needles are used for administering medication or withdrawing fluid from the body of a patient. Such disposable medical devices typically include blood-collecting needles, fluid handling needles, and assemblies thereof. Current medical practice requires that fluid containers and medical needles used in such devices be inexpensive and readily disposable. Existing blood collection devices often employ some form of durable, reusable holder on which detachable and disposable medical needles and fluid collection tubes may be mounted. A blood collection device of this nature may be assembled prior to use and then discarded after use.

A blood collection device or intravenous (IV) infusion device typically includes a needle cannula having a proximal end, a pointed distal end, and a lumen extending therebetween. The proximal end of the needle cannula is securely mounted in a plastic hub defining a central passage that communicates with the lumen extending through the needle cannula. A thin, flexible thermoplastic tubing is connected to the hub and communicates with the lumen of the needle cannula. The end of the flexible plastic tubing remote from the needle cannula may include a fixture for connecting the needle cannula to a fluid collection tube holder or other receptacle. The specific construction of the fixture will depend upon the characteristics of the receptacle to which the fixture is to be connected.

In order to reduce the risk of incurring an accidental needle-stick wound, protection of used needle cannulas becomes important. With concern about infection and transmission of diseases, methods and devices to enclose or cover the used needle cannula have become very important and in great demand in the medical field. For example, needle assemblies often employ a safety shield that can be moved into shielding engagement with a used needle cannula to minimize risk of an accidental needle stick.

Prior art devices in this area often include flexible wings, which are used as means for securing the needle assemblies to the body of a patient during a medical procedure. Winged needle assemblies typically include a barrel or body portion, a wing portion mounted to the body portion, and a needle cannula. The wing portion can be used to manipulate the assembly during insertion and withdrawal of the needle cannula from the patient. The wing portion is also used to stabilize the assembly against the patient's skin, by providing a surface area for taping, attachment, etc. to the patient to prevent movement of the assembly.

U.S. Pat. No. 7,294,118 to Saulenas et al. discloses a retractable push-button needle assembly, in which a needle is attached to a hub and extends through a barrel. A push-button actuator extends from the hub and is in interference engagement with the barrel. Activation is accomplished with a user actively pushing the push-button into the barrel, thereby causing the needle to retract within the barrel under power of a spring disposed between the hub and the barrel.

Needle assemblies may also incorporate passively activated safety features. In such devices, the needle shielding feature is passively actuated upon normal usage of the device. For example, the activation of the safety feature may automatically occur, such as upon removing an outer safety packaging cover and after releasing the user's grip on the device after insertion of the needle into the patient's injection site. The safety feature may be a safety shield that is propelled toward the needle tip, or a force that is exerted on the needle to retract the needle into the body of the device. U.S. Pat. No. 6,682,510 to Niermann discloses a passive safety blood collection set which includes a tip guard slidably movable along a needle cannula. The tip guard is mounted to a needle hub through a pair of collapsible leaves, which are collapsed onto themselves and held in place by a packaging cover. In use, the practitioner holds the leaves in the collapsed or folded state to remove the cover, and then releases the leaves enabling them to unfold to propel the tip guard distally.

Such passively actuated devices typically involve a relative axial force between the needle and the shield for activation of the safety feature. If this relative axial force is greater than a resisting force supplied by the friction between the needle and the patient's tissue, the needle may be self-ejected from the patient during activation of the safety feature.

SUMMARY OF THE INVENTION

A need exists for a blood collection set including a shielding needle assembly that achieves secure and effective shielding of a used needle cannula. An additional need exists for a blood collection set with a shielding needle assembly that is passively operated, and such that the activation of the safety feature does not cause the needle cannula to be self-ejected from the patient. A further need exists for a passively operated shielding needle assembly that provides a guide to help in locating an ideal puncture site.

A safety needle device is provided including a hub having a needle cannula with a puncture tip extending from a forward end thereof, and a shield member in telescoping association with the hub. The hub and the shield member are adapted for relative telescopic movement with respect to each other between a first position in which the puncture tip of the needle cannula is exposed from a forward end of the shield member, and a second position in which the puncture tip of the needle cannula is encompassed within the shield member. A drive member is disposed between the hub and the shield member and is capable of biasing the hub and the shield member telescopically away from each other, i.e., toward the second position. A contact member maintains the hub and the shield member in the first position against the bias of the drive member with the needle cannula exposed from a forward end of the shield member. The contact member comprises a lever in pivotal engagement with the shield member including a forward portion adjacent the puncture tip of the needle cannula and a rearward portion including structure to releasably maintain the hub and the shield in the first position. The contact member is movable during contact with a patient's skin surface, thereby permitting release of the hub and the shield member from the first position and permitting the drive member to bias the hub and the shield member toward the second position.

In one embodiment, release of the contact member from the patient's skin surface permits the drive member to bias the hub and the shield member telescopically away from each other fully to the second position with the puncture tip of the needle cannula encompassed within the shield member.

The rearward portion of the lever of the contact member may include a first engagement portion for engaging with the hub to maintain the hub and the shield in the first position, with the first engagement portion being releasable from engagement with the hub upon pivotal movement of the lever during contact with a patient's skin surface. The rearward portion of the lever may further include a second engagement portion for engaging with the hub upon pivotal movement of the lever during contact with a patient's skin surface to maintain the hub from being biased entirely to the second position when the first engagement member is released from engagement with the hub. The second engagement portion may be releasable from engagement with the hub upon pivotal movement of the lever in a reverse direction during release of contact with a patient's skin surface.

A further embodiment of the invention is directed to a shielding needle assembly comprising a needle cannula having a puncture tip at a distal end thereof and with a needle hub supporting the needle cannula. The needle hub is disposed within the passage of a barrel extending between a proximal end and a distal end. A drive member, such as a coil spring, is further disposed between the barrel and the needle hub for driving the needle hub from a first position in which the puncture tip of the needle cannula is exposed from the distal end of the barrel to a second position where the puncture tip of the needle cannula is disposed entirely within the barrel. A lever is pivotally connected to the barrel and includes a forward portion adapted to contact a patient's skin surface and a rearward portion including a releasable engagement with the needle hub for maintaining the needle hub in the first position. Contact of the forward portion of the lever with a patient's skin surface pivots the lever and releases an initial engagement with the needle hub at the rearward portion of the lever.

The rearward portion of the lever may include a first engagement portion engaging a portion of the needle hub for maintaining the needle hub in the first position. In this manner, contact of the forward portion of the lever with the patient's skin and/or insertion of the needle cannula through the patient's skin causes the lever to pivot with respect to the barrel such that the first engagement portion of the lever disengages from the needle hub. Moreover, the rearward portion of the lever may further include a second engagement portion for engagement with the needle hub. In this manner, contact of the forward portion of the lever with the patient's skin and/or insertion of the needle cannula through the patient's skin causes the lever to pivot with respect to the barrel such that the first engagement portion of the lever disengages from the needle hub and the second engagement portion of the lever maintains the needle hub in a position with the puncture tip extending from the forward end of the barrel. Further, the second engagement portion of the lever disengages from the needle hub upon pivotal movement of the lever with respect to the barrel in a reverse direction during removal of the forward portion of the lever from the patient's skin surface, such as during removal of the needle cannula from the patient's skin. In this manner, the drive member drives the needle hub to a position wherein the puncture tip of the needle cannula is disposed entirely within the barrel.

The lever may be integrally molded with the barrel, or may be a separate element which is pivotally connected to the barrel, such as through a pivot pin. Desirably, the front portion of the pivoting lever may be configured to interface a patient's point of injection by straddling the puncture tip of the needle cannula, and may include a slotted pad.

In a further embodiment of the invention, a blood collection set includes such a shielding needle assembly, with a flexible tubing extending from the needle hub, and with an opposed end of the flexible tubing adapted for connection to a receptacle for accommodating a blood collection tube. For example, the opposite end of the flexible tube may include a non-patient needle cannula, or may include a fitting including a female luer fitting which is adapted to be mated with a separate member including a non-patient needle cannula.

A further embodiment involves a method of actuating a needle assembly. A needle assembly is provided comprising a hub including a needle cannula with a puncture tip extending from a forward end thereof, with the hub at least partially disposed within a shield member and biased toward a position in which the puncture tip of the needle cannula is encompassed within the shield member. The needle assembly further comprises a pivotal lever connected to the barrel and including a first engagement with the hub for maintaining the hub against the bias with the puncture tip exposed from a forward end of the shield. The method involves inserting the puncture tip of the needle cannula through the skin of a patient such that the pivotal lever contacts the patient's skin surface and causes the lever to pivot with respect to the shield member, thereby releasing the first engagement between the lever and the hub.

The inserting step may further entail engaging a second engagement between the lever and the hub upon release of the first engagement. Moreover, the method may further comprise a step of removing the puncture tip of the needle cannula from the skin of the patient such that the pivotal lever releases from contact with the patient's skin surface and pivots with respect to the shield member in an opposite direction. In this manner, the second engagement between the lever and the hub is released, permitting the hub to be biased toward a position in which the puncture tip of the needle cannula is encompassed within the shield member.

Further details and advantages of the invention will become apparent upon reading the following detailed description in conjunction with the accompanying drawings, wherein like reference numerals identify like parts throughout.

BRIEF DESCRIPTION OF THE DRAWINGS

FIG. 5 is an exploded perspective view of portions of the needle assembly depicted in connection with the embodiment of FIG. 1.

FIG. 6 is a perspective view of the needle assembly of FIG. 5 in an assembled condition.

DETAILED DESCRIPTION OF THE PRESENT INVENTION

Figure 1:
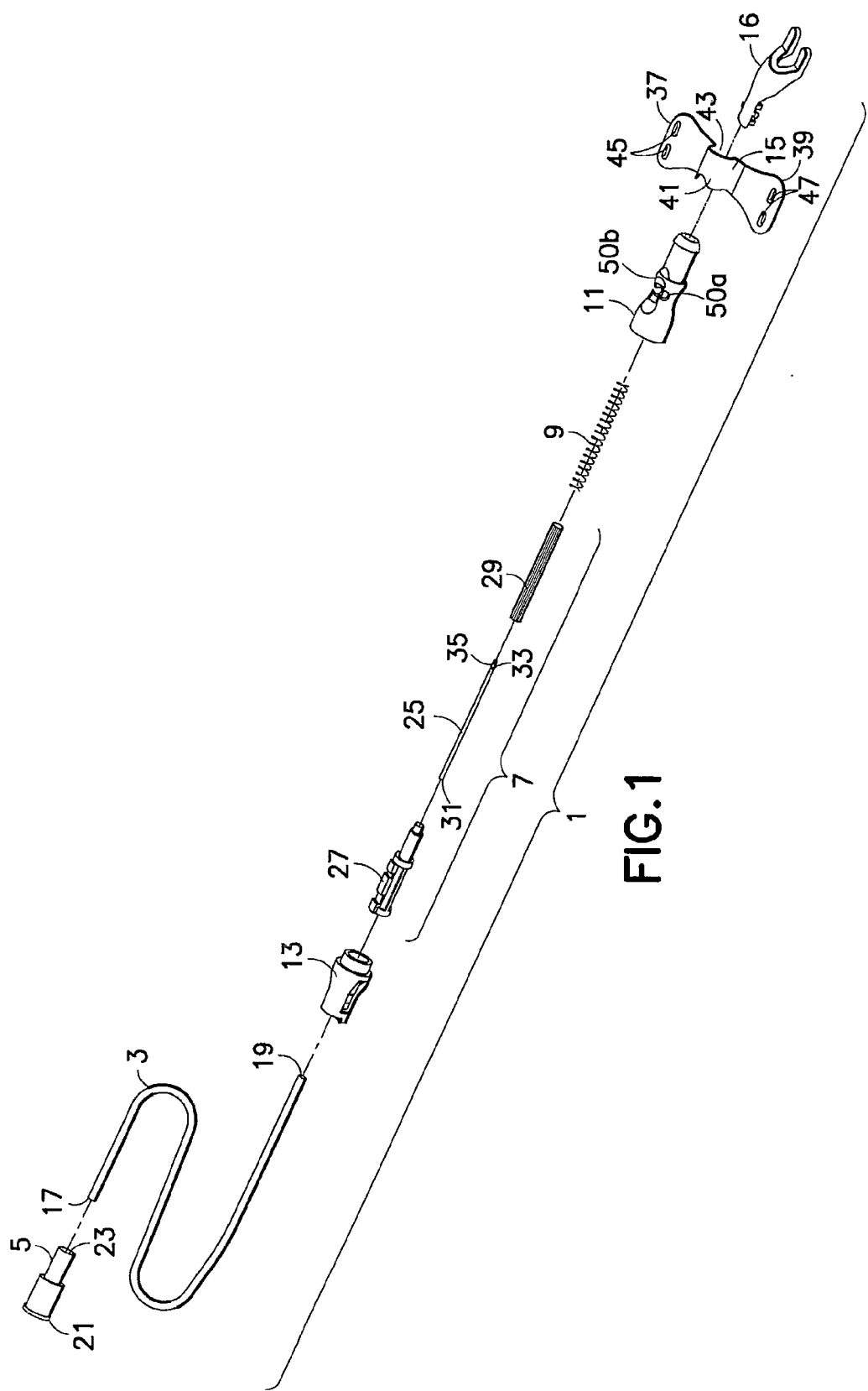
FIG. 1 is an exploded perspective view of a blood collection set including a shielding needle assembly in accordance with an embodiment of the present invention.

For purposes of the description hereinafter, the words "upper", "lower", "right", "left", "vertical", "horizontal", "top", "bottom", "lateral", "longitudinal", and like spatial terms, if used, shall relate to the described embodiments as oriented in the drawing figures. However, it is to be understood that many alternative variations and embodiments may be assumed except where expressly specified to the contrary. It is also to be understood that the specific devices and embodiments illustrated in the accompanying drawings and described herein are simply exemplary embodiments of the invention.

Generally, an embodiment of the invention relates to a passive retracting needle assembly with a pivoting skin sensor lever. The skin sensor lever is intended to sense the action of needle insertion and removal by a healthcare professional and passively activate the safety device after those two occurrences are completed, without the need for any other conscious action by the health care professional. The activation of the safety device does not create a relative axial force that is great enough to cause the needle cannula to be self-ejected from the patient. Furthermore, the skin sensor lever may provide a guide to help in locating a puncture site, and may distract needle-phobic patients from the negative visual impact of a bare needle. The invention is generally described in terms of a shielding needle assembly for use in a blood collection or infusion set, and encompasses the needle assembly as well as such a collection or infusion set.

Figure 2:
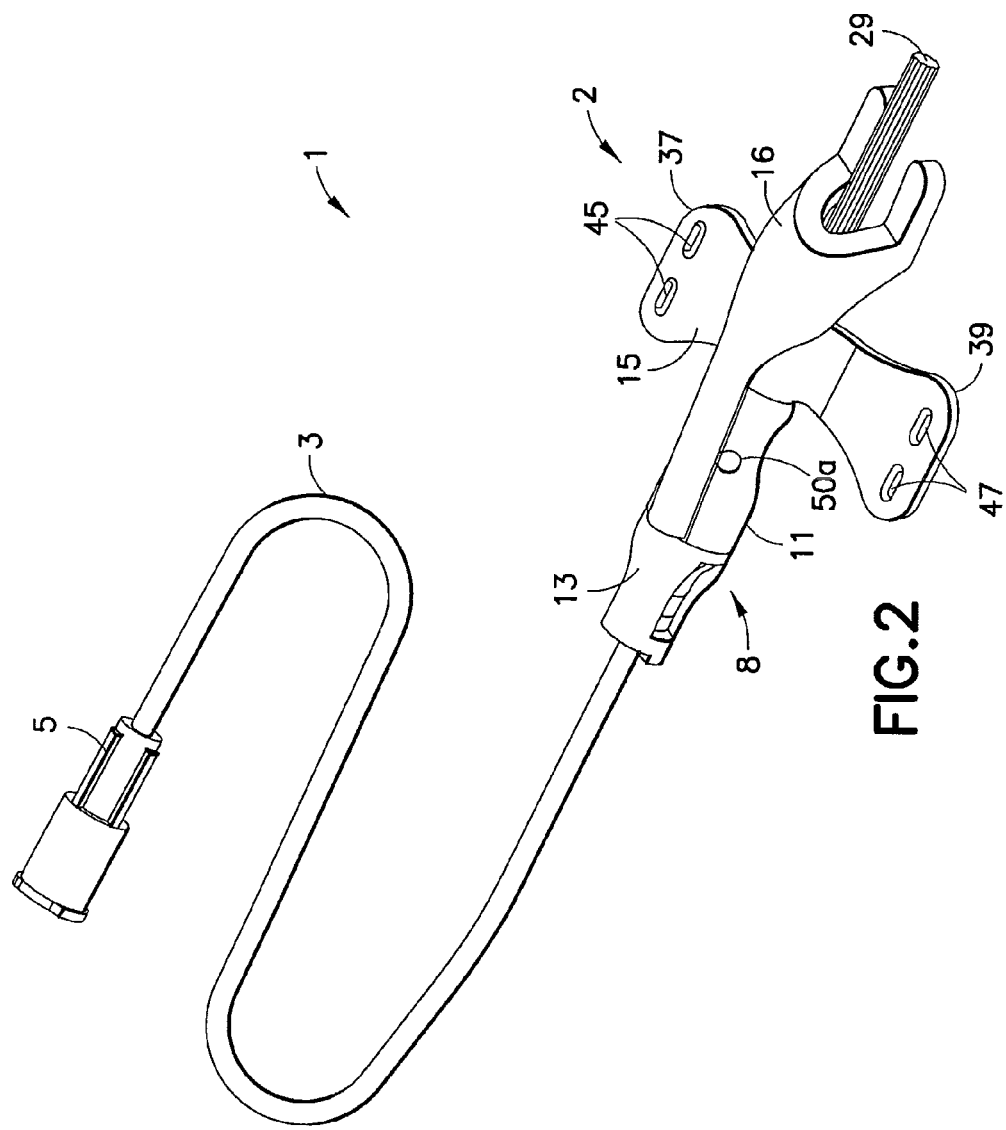
FIG. 2 is a perspective view of the assembly of FIG. 1 in an assembled condition.

As shown generally in FIGS. 1 and 2, a fluid collection/infusion set is shown as blood collection set 1 including a safety shielding needle device or assembly 2, flexible tubing 3 extending from the needle device or assembly 2, and a protective cap or shield such as needle protector 29 forming a packaging cover removably mounted to the needle assembly 2 opposite flexible tubing 3, such as through frictional engagement therewith. A first end or proximal end 17 of flexible tubing 3 is adapted for connection with a receptacle such as for blood collection, while needle assembly 2 extends from a second end or distal end 19 of flexible tubing 3.

Tubing 3 includes proximal end 17, distal end 19, and a passage extending between the ends. Tubing 3 may be conventional intravenous tubing used in conventional blood collection sets. Proximal fitting 5 is molded unitarily from a plastic material and includes a proximal end 21, a distal end 23, and a passage extending between the ends. Portions of the passage adjacent distal end 23 are configured to telescope tightly over proximal end 17 of tubing 3 so that the passage through tubing 3 communicates with the passage through proximal fitting 5. Proximal end 21 of fitting 5 may define, for example, a female luer connector that can be mated with an appropriate male luer connector to infuse a medication into a patient. For example, a male luer connector at the distal end of a conventional syringe may be connected directly to proximal fitting 5 for infusing a medication into the patient. In this instance, a separate male luer cap can be provided for closing proximal fitting 5. Alternatively, fitting 5 may be adapted to accommodate a non-patient needle assembly including an elastomeric sheath, such as through a male luer connector hub engaged with fitting 5, as is known in the art. In such an embodiment, a conventional needle holder may be fitted with the non-patient needle so as to be placed in communication with an evacuated blood collection tube, thereby providing a blood collection assembly in known manner. Other fittings may be engaged with proximal fitting 5 in accordance with the specific intended use of collection/infusion set 1. Additionally, connectors of other configurations may be employed to achieve a particular objective.

As noted, blood collection set 1 includes a needle device or assembly 2 extending from flexible tubing 3. With general reference to FIGS. 1 and 2, one embodiment of the invention defines the shielding needle assembly 2 as generally including a needle portion 7 including a needle cannula 25 in connection with a needle hub 27, a safety shield member 8 including a barrel assembly comprising a front barrel 11, a rear barrel 13, and a winged structure 15, a drive member such as spring 9 for moving the needle portion and the shield member with respect to each other, and a contact member such as skin sensor lever 16.

With reference to FIGS. 2-7, needle portion 7 includes a needle cannula 25, a needle hub 27 and, optionally, a needle protector 29. Needle protector 29 may be shaped to interfere with the pivotal movement of pivoting skin sensor lever 16 allowing lever 16 to be restrained in a downward position during transit and storage. Needle cannula 25 has a proximal end 31, a distal end 33, and a lumen extending between the ends. Distal end 33 of needle cannula 25 is beveled to a sharp puncture tip 35, such as an intravenous puncture tip. Puncture tip 35 is provided for insertion into a patient's blood vessel, such as a vein, and is therefore designed to provide ease of insertion and minimal discomfort during venipuncture.

Needle hub 27 may be molded unitarily from a plastic material such as polycarbonate, polypropylene, polyethylene, acrylic, polystyrene, and ABS. Needle hub 27 may be molded from a transparent or translucent material to enable observation of blood or other fluid flowing through needle hub 27. Needle hub 27 includes a rearward or proximal end 59, a forward or distal end 61, and a passage extending between the ends. Portions of the passage adjacent proximal end 59 are dimensioned to receive distal end 19 of tubing 3. More particularly, distal end 19 of tubing 3 may be telescoped into the passage of needle hub 27 and bonded in position adjacent proximal end 59 of needle hub 27. Portions of the passage adjacent distal end 61 of needle hub 27 may be dimensioned for slidable receipt of proximal end 31 of needle cannula 25.

Figure 7:
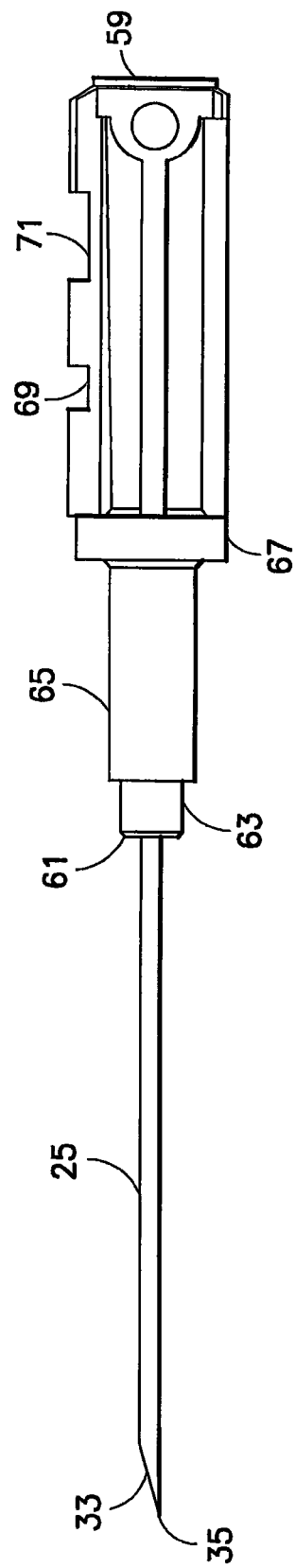
FIG. 7 is a side view of the needle assembly of FIG. 5 without a needle protector on the needle cannula.
Figure 8:
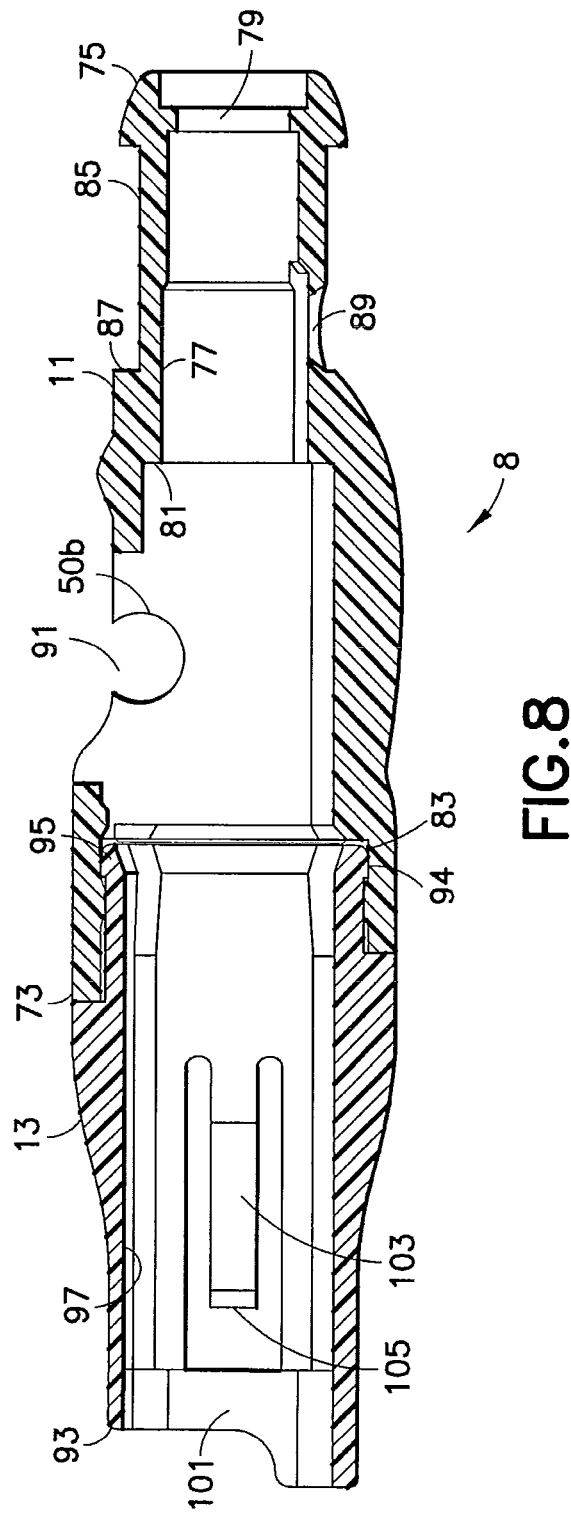
FIG. 8 is a longitudinal cross-sectional view of a housing of the needle assembly of FIG. 1.
Figure 9:
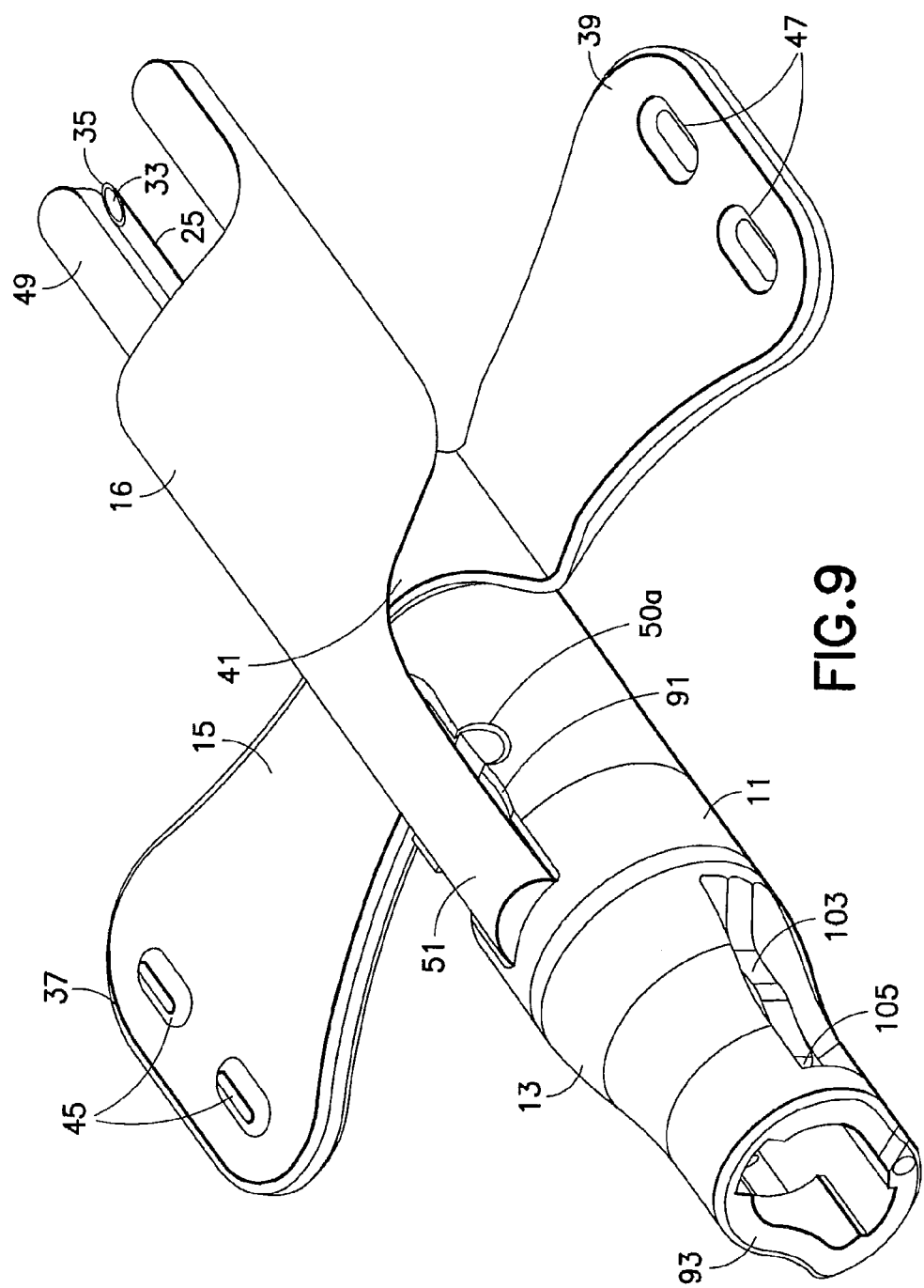
FIG. 9 is a perspective view of the needle assembly of FIG. 1 in an initial state showing a needle cannula projecting from the housing.
Figure 10:
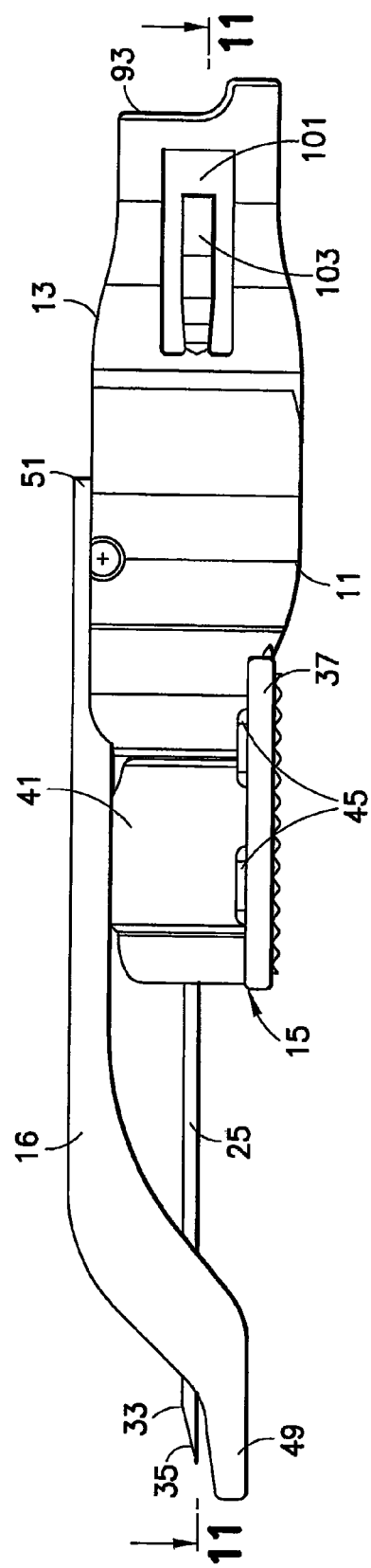
FIG. 10 is a side view of the needle assembly of FIG. 9.
Figure 14:
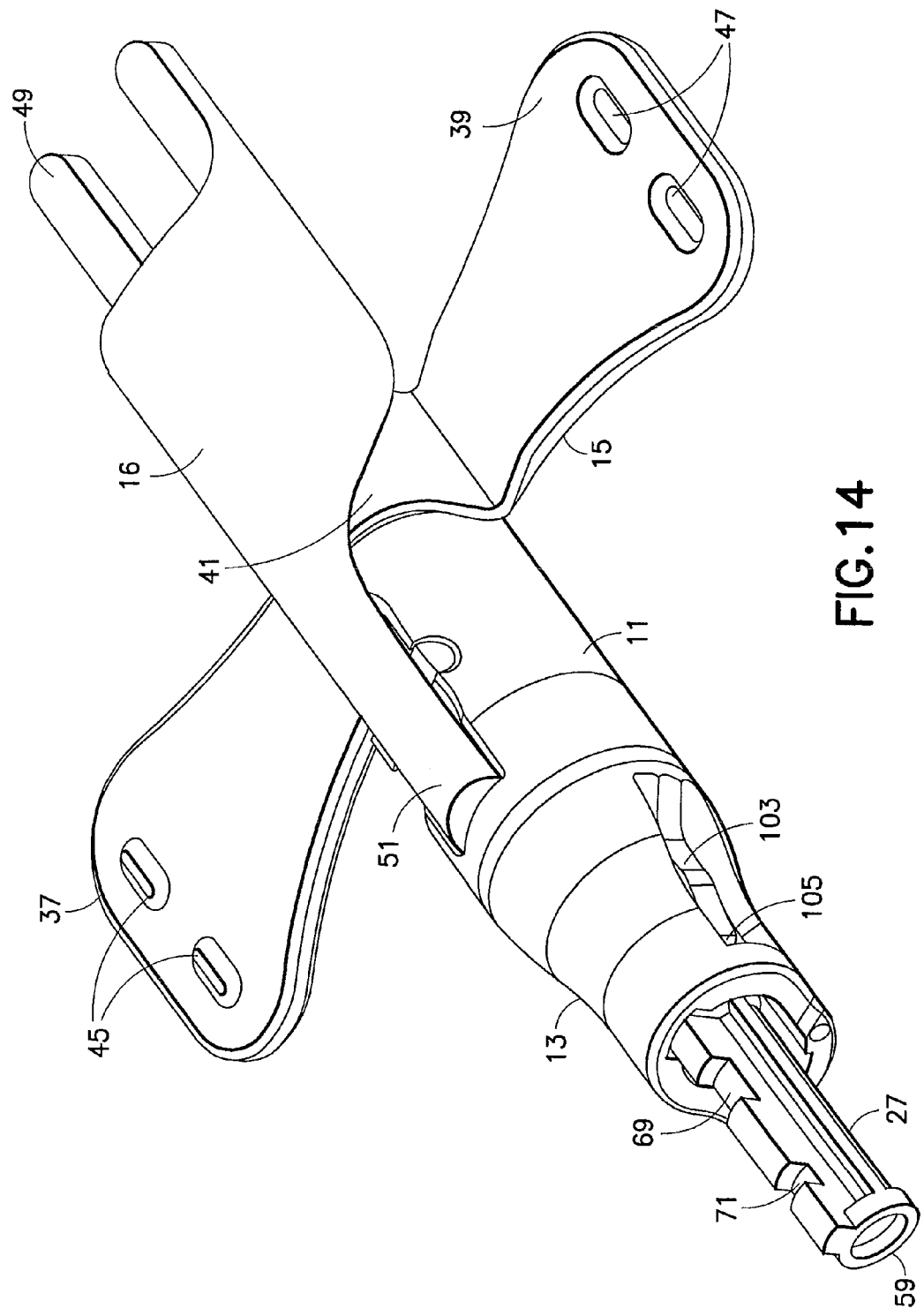
FIG. 14 is a perspective view of the needle assembly shown in FIG. 1 with the needle cannula in a retracted position.

With reference to FIG. 8, and with continuing reference to FIGS. 2-7, shield member 8 is in telescoping association with needle portion 7, and in particular with needle hub 27, with at least one of needle hub 27 and/or shield member 8 adapted for relative telescopic movement with respect to the other. In particular, needle hub 27 and shield member 8 are axially movable with respect to each other between a first position in which puncture tip 35 of needle cannula 25 is exposed from the forward end of shield member 8 as shown in FIG. 9, and a second position in which puncture tip 35 of needle cannula 25 is encompassed within shield member 8, as shown in FIG. 14. This may be accomplished by providing needle hub 27 in slidable engagement within shield member 8.

Shield member 8 is generally tubular or cylindrical in shape, and may be a unitary structure, desirably molded from a thermoplastic material. In one embodiment, shield member 8 comprises a barrel assembly including a front barrel 11, a rear barrel 13, and a winged structure 15. Front barrel 11 may be a substantially tubular unitarily molded plastic structure with opposite proximal and distal ends 73 and 75, and a passage 77 extending between the ends. Rear barrel 13 may also be a substantially tubular structure with a proximal end 93, a distal end 95, and a passage 97 extending between the ends. Passage 77 of front barrel 11 is defined further by an annular locking rib 83 near proximal end 73, while exterior portions of rear barrel 13 adjacent distal end 95 define an annular locking ring 94. Locking rib 83 and locking ring 94 permit locked engagement of front and rear barrels 11 and 13. In particular, locking ring 94 is configured for snapped locked engagement with annular locking rib 83 in passage 77 of front barrel 11 to engage front and rear barrels 11 and 13 with one another. The engagement of front and rear barrels 11 and 13 can be made more permanent by adhesive bonding, welding, or by increasing the interference between annular locking rib 83 and locking ring 94. Alternately, front barrel 11 and rear barrel 13 may be connected by threaded engagement where one of front or rear barrels 11 and 13 has external threads and the other of front and rear barrel 11 and 13 has internal threads.

Front barrel 11 includes an annular step 81 within passage 77. Annular step 81 defines an inside diameter less than the outside diameter of flange 67 on needle hub 27. Thus, annular step 81 defines a fixed limit for distal movement of needle hub 27 in front barrel 11. Likewise, proximal portions of passage 97 through rear barrel 13 are characterized by an inwardly extending proximal flange 101. Proximal flange 101 has an inside diameter less than the outside diameter of flange 67 on needle hub 27. Thus, proximal flange 101 limits proximal movement of needle hub 27 in rear barrel 13.

As noted, needle hub 27 and shield member 8 are axially movable with respect to each other. The needle assembly 2 further includes a drive member such as spring 9 extending between the needle hub 27 and the shield member 8, providing a biasing force to bias the needle hub 27 and the shield member 8 axially or longitudinally away from each other. Drive member or spring 9 is generally coaxially positioned with the shield member 8 and/or the needle hub 27, with the needle assembly 2 in the first position. The drive member may be in the form of a coil compression spring or like biasing element and is generally adapted to move the shield member 8 and/or the needle hub 27 with respect to each other between the first position and the second position of needle assembly 2. The biasing force of the drive member is described herein in terms of biasing the needle hub 27 and shield member 8 with respect to each other, such as a biasing force biasing the needle hub 27 and shield member 8 axially away from each other. It is noted that actuation of the needle assembly 2 is based on this biasing force of the drive member causing movement of either the needle hub 27 and shield member 8, or movement of both the needle hub 27 and shield member 8 with respect to each other. For example, if the user is holding the needle hub 27 during activation, the biasing member will cause the shield member 8 to extend or move distally with respect to needle hub 27 to the second shielding position of needle assembly 2. On the other hand, if the user is holding the shield member 8 during activation, the biasing member will cause the needle hub 27 to retract or move proximally with respect to shield member 8 to the second shielding position of the needle assembly 2.

Figure 11:
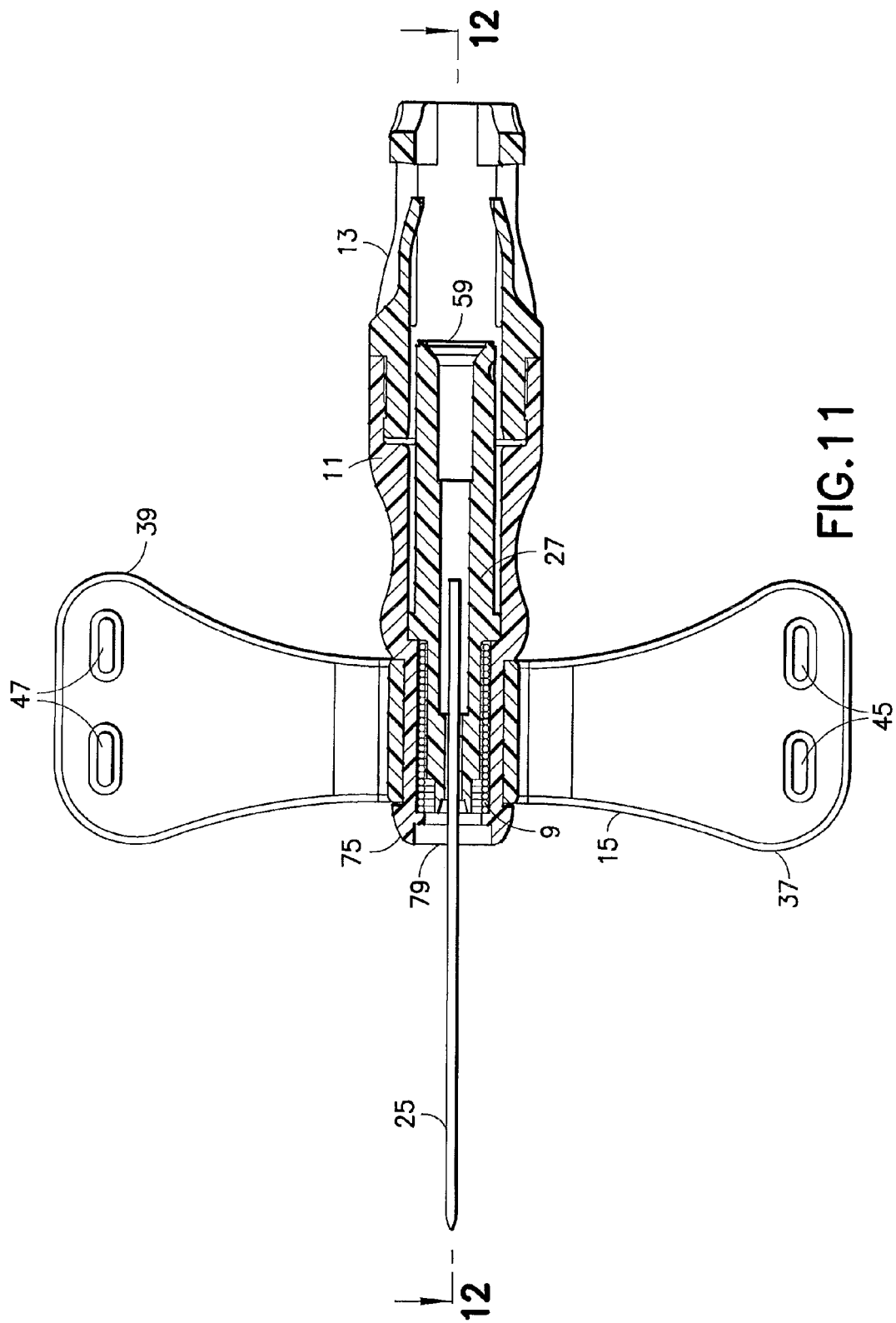
FIG. 11 is a top cross-sectional view taken along line 11-11 in FIG. 10.
Figure 12:
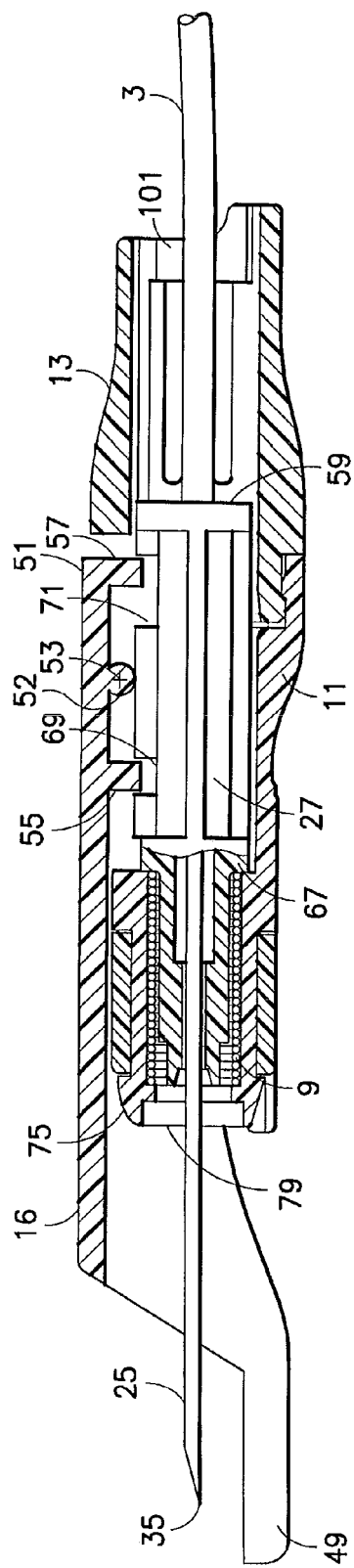
FIG. 12 is a side cross-sectional view taken along line 12-12 in FIG. 11.

As depicted in the figures and with specific reference to FIGS. 1 and 11, the drive member in the form of spring 9 has a first end which is generally disposed about the needle hub 27, and a second end which is generally in contact with a portion of the shield member 8. For example, external portions of needle hub 27 adjacent distal end 61 may define a small diameter cylindrical tip 63, with an intermediate diameter cylindrical spring mounting section 65 extending proximally from small diameter cylindrical tip 63, and a larger diameter cylindrical flange 67 extending outwardly at proximal end of spring mounting section 65. Flange 67 defines a limit for proximal movement of spring 9 on needle hub 27 and a limit for distal movement of needle hub 27 relative to front barrel 11. Further, portions of passage 77 near distal end 75 of front barrel 11 may define an inwardly extending annular distal flange 79 with an inside diameter less than the outside diameter of spring 9. Thus, distal flange 79 defines a distal stop for spring 9 and enables spring 9 to be compressed within front barrel 11. Annular step 81 is spaced from distal flange 79 by a distance substantially equal to the compressed length of spring 9. Thus, the section of passage 77 between distal flange 79 and annular step 81 effectively defines a spring housing.

In a general sense, needle hub 27 and shield member 8 are maintained from movement with respect to each other against the biasing force of spring 9 to maintain needle assembly 2 in the first position with puncture tip 35 extending from the forward end of the shield through distal end 75 of front barrel 11. Needle hub 27 and shield member 8 may be maintained in this manner through a releasable engagement adapted to maintain the needle hub 27 and the shield member 8 in position with respect to each other against the biasing force of spring 9. For example, needle hub 27 and shield member 8 may include interengaging structure which provides an engagement between the needle hub 27 and the shield member 8 to prevent the spring 9 from biasing the needle hub 27 and the shield member 8 away from each other in a longitudinal direction, such as through pivoting skin sensor lever 16.

Figure 3:
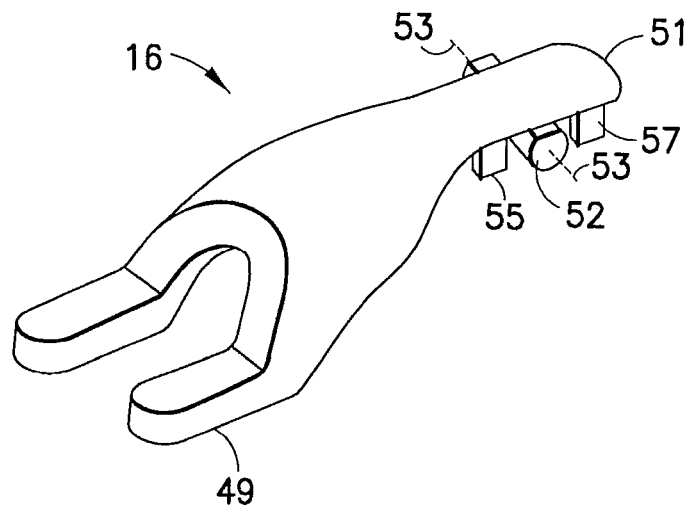
FIG. 3 is a perspective view of the skin sensor of the assembly of FIG. 1.
Figure 4:
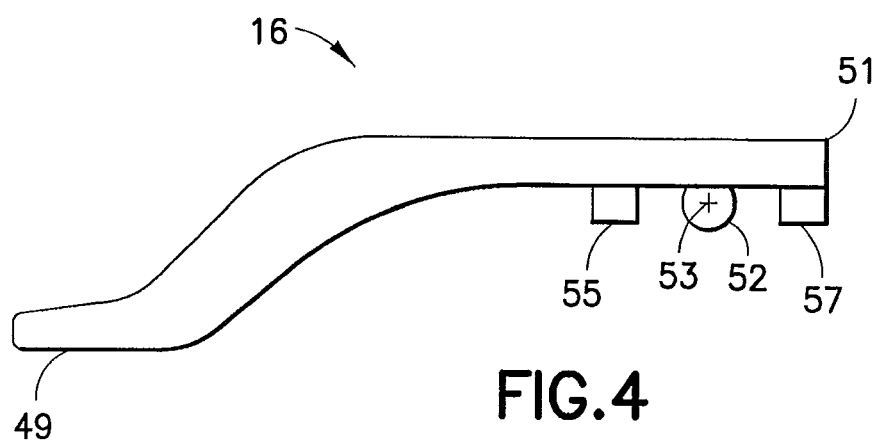
FIG. 4 is a side plan view of the skin sensor of FIG. 3.

With reference to FIGS. 3 and 4, and with continuing reference to FIGS. 1 and 2, pivoting skin sensor lever 16 includes a front portion 49 and a rear portion 51. Pivoting skin sensor lever 16 is attached to front barrel 11 forming a pivot axis 53 substantially perpendicular to an axis of front barrel 11, needle hub 27, and needle cannula 25. Pivot axis 53 is generally located adjacent the upper surface of front barrel 11. Front portion 49 of lever 16 may be adapted so as to interface with the patient's point of injection by straddling needle cannula 25. Front portion 49 of pivoting skin sensor lever 16 may further include a slotted pad. The slotted pad offers more surface area and comfort to the patient. Desirably, pivoting skin sensor lever 16 pivots about pivot axis 53 such that front portion 49 moves in an up and down manner, with the up direction being away from the patient's point of injection and the down direction being toward the point of injection. Rear portion 51 also moves in an up and down manner, opposite to front portion 49 by virtue of the location of pivot axis 53.

Rear portion 51 of lever 16 interfaces with needle hub 27 to maintain needle hub 27 against the bias of spring 9. In particular, needle hub 27 is configured to include a first recess 69 and a second recess 71 as shown in FIGS. 5-7. First recess 69 and second recess 71 are designed to interact with first engagement member 55 and second engagement member 57 of pivoting skin sensor lever 16, respectively, in order to retain needle hub 27 in a forward position against the force of spring 9, as will be discussed in more detail herein.

Front barrel 11 further includes an opening 91 extending through the top wall surface thereof and communicating with passage 77. Opening 91 is dimensioned and configured to receive rear portion 51 of pivoting skin sensor 16 allowing the first engagement member 55 and the second engagement member 57 to interact with first recess 69 and second recess 71, respectively, of needle hub 27.

In one embodiment, pivot axis 53 may be formed through a lever bar arrangement, whereby pivoting skin sensor lever 16 is connected to front barrel 11 through a pin and hole arrangement. For example, pin 52 may be integrally formed on the underside of lever 16, as shown in FIGS. 3 and 4. Pin 52 may be positioned at any location along lever 16, and is desirably positioned between first engagement member 55 and second engagement member 57. Pin 52 is desirably cylindrical in cross-section. In order to form pivot axis 53 between lever 16 and front barrel 11 and to provide a mechanism for attachment of lever 16 thereto, front barrel 11 is further provided with structure forming a corresponding guide surface for accommodating pin 52 in a pivotal manner through opening 91. For example, portions of the wall forming front barrel 11 may be cut away at opposing lateral sides thereof so as to accommodate pin 52 therein. As shown in FIGS. 1, 2, and 9, such cutaway portions of the wall of front barrel 11 may be profiled so as to form guide surfaces 50a and 50b on opposing lateral sides thereof. Guide surfaces 50a and 50b act as a resting surface for pin 52 of lever 16, thereby providing a mechanism for attaching and retaining lever 16 to front barrel 11, such as through a snap-fit engagement therewith, and provide a hinge-like engagement for pivoting about pivot axis 53.

In an alternate embodiment, it is further contemplated that front barrel 11 may be formed with a forward shoulder and a rearward shoulder spaced from each other, and each including a surface profile for accommodating the outer surface of pin 52. The spacing of the forward and rearward shoulders forms a guide surface therebetween for accommodating an outer surface of pin 52 in a hinge-like, pivotal manner. The forward and rearward shoulders may be integrally formed within the internal surface of front barrel 11, and may individually represent a continuous structure extending across opening 91. Alternatively, each of the forward shoulder and rearward shoulder may be partial shoulder structures extending from opposing sides of the internal surface of front barrel 11 at opposing sides of opening 91, thereby providing a guide surface for accommodating an outer surface of pin 52.

Alternatively, pivoting skin sensor lever 16 may be integrally molded directly to a portion of front barrel 11. For example, one or more thin flexible members may be provided to create a living hinge which is integral with front barrel 11.

The outer circumferential surface of front barrel 11 may be defined by an annular wing-mounting undercut 85 near distal end 75. Annular undercut 85 is provided with detents 87 for positioning winged structure 15 in a fixed rotational orientation on front barrel 11. Winged structure 15 is typically molded unitarily from an elastic material such as polyolefin, polyvinyl chloride, or other such elastomeric polymers. Winged structure 15 includes flexible side panels 37 and 39 and a tubular mount 41. Tubular mount 41 includes an interior passage 43 that is dimensioned for snug engagement over front barrel 11. Panels 37 and 39 are molded with a top surface that is relatively smooth. However, the top surface of panel 37 includes a pair of arcuate projections 45 at portions remote from tubular mount 41. The top surface of panel 39 includes a pair of arcuate recesses 47 that are dimensioned, disposed, and configured to receive projections 45 on panel 37 when panels 37 and 39 are folded so that the top surfaces thereof are in face-to-face engagement with one another. The interengagement of projections 45 with recesses 47 ensures that folded panels 37 and 39 function as a handle without slipping relative to one another. The bottom surfaces of panels 37 and 39 may be provided with a plurality of tactile bumps (not shown). The tactile bumps facilitate gripping of folded panels 37 and 39 between a thumb and forefinger of the user. The color of the winged structure 15 may designate the gauge of the needle cannula 25. Alternate embodiments where winged structure 15 has only one side panel 37 or 39 are contemplated to provide an alternate means to manipulate the needle assembly by the user.

Annular undercut 85 of front barrel 11 may further have a dampening agent injection port 89 for injecting a dampening agent into passage 77. Dampening agent injection port 89 may then be covered by winged structure 15.

Rear barrel 13 may further include resiliently deflectable locking fingers 103 that are cantilevered proximally and inwardly from opposed locations on rear barrel 13. Each locking finger 103 includes a proximal end 105 that is spaced from proximal flange 101 by a distance equal to or slightly greater than the axial thickness of flange 67 on needle hub 27. Hence, flange 67 can be trapped between the distal surface of stop flange 101 and locking fingers 103. Proximal ends 105 of locking fingers 103 are spaced from one another by a distance less than the diameter of flange 67 on needle hub 27.

With reference to FIG. 9, and with continuing reference to FIGS. 1-8, fluid collection/infusion set 1 is assembled by first constructing needle portion 7. Needle portion 7 is constructed by mounting proximal end 31 of needle cannula 25 into the passage of needle hub 27. Needle cannula 25 may be secured in this position by an adhesive, such as a heat curable or ultraviolet cured epoxy. Needle cannula 25 is oriented such that puncture tip 35 at distal end 33 of needle cannula 25 and winged structure 15 are symmetrical about a common plane. Distal end 19 of tubing 3 is then secured in the proximal end 59 of needle hub 27. Tubing 3 may be secured in this position by solvent bonding, adhesive bonding, or welding.

Assembly continues by telescoping spring 9 over spring mounting section 65 of needle hub 27. Needle portion 7 and spring 9 are then aligned and telescoped in a distal direction into front barrel 11 thus compressing spring 9. The rear portion 51 of pivoting skin sensor 16 is then positioned in opening 91 of front barrel 11 allowing first engagement member 55 and second engagement member 57 to interact with the forward recess 69 and rearward recess 71, respectively, of needle hub 27. The interaction between engagement members 55 and 57 and recesses 69 and 71 retains needle hub 27 in a forward position against the force of compressed spring 9. Pivoting skin sensor 16 is positioned to form a pivot axis 53 that is perpendicular to front barrel 11, needle hub 27, and needle cannula 25. Pivot axis 53 may be created by a pin and hole arrangement or, alternatively, pivoting skin sensor lever 16 may be integrally molded to front barrel 11 to form a quasi-hinge.

Winged structure 15 is then mounted over distal end 75 of front barrel 11. Interior passage 43 of tubular mount 41 of winged structure 15 is aligned with detents 87 on front barrel 11. Thus, a snug fit of tubular mount 41 of winged structure 15 is achieved with annular undercut 85 and detents 87 to hold winged structure 15 on front barrel 11 and to prevent rotation. In this mounted condition, panels 37 and 39 of winged structure 15 define a plane extending substantially normal to the plane of symmetry defined by puncture tip 35 at distal end 33 of needle cannula 25 and pivoting skin sensor lever 16.

Assembly further continues by threading distal end 19 of tubing 3 through rear barrel 13. Sufficient distal movement of rear barrel 13 along tubing 3 enables locked engagement of distal end 95 of rear barrel 13 within proximal end 73 of front barrel 11. Proximal fitting 5 can then be secured to proximal end 17 of tubing 3.

When a viscous dampening agent is used, the passage 77 of front barrel 11, the spring mounting section 65 of needle hub 27, and the distal surface of the flange 67 on needle hub 27 define a chamber that constrains the preferred location of the dampening agent. An injection port 89 located within the sidewall of front barrel 11 is used for dispensing the viscous dampening agent into the chamber. The dampening agent may be injected through a dispensing cannula that has a distal end shaped to fit within injection port 89. It is also contemplated that the dampening agent can be applied to passage 77, spring 9, needle hub 27, or any of the three components prior to assembly to produce an alteration to retraction speed or velocity.

The viscous dampening agent may be a silicone that functions to dampen the velocity of needle hub 27 relative to front barrel 11 and rear barrel 13. The viscous dampening agent creates a resistance to slow the retraction of needle hub 27 and needle cannula 25. An example of a dampening agent is a thixotropic gel, similar to the type of gel used as a separator gel in blood collection tubes. A thixotropic gel used as a dampening agent provides unique properties relative to spring 9. In particular, the thixotropic gel exhibits the ability to temporarily and elastically bond adjacent coils of spring 9 together. Initiation of retraction releases the stored energy of spring 9, and permits spring 9 to expand. The thixotropic gel creates resistance similar to silicone, and hence dampens the velocity of hub 27 and needle cannula 25. However, unlike conventional silicone, the temporary bonding between adjacent coils achieved by the thixotropic gel provides a slower initial acceleration. The slower initial acceleration results in a significant reduction in splatter during retraction of needle cannula 25. While the use of thixotropic gel was described herein above as a dampening agent, this is not to be construed as limiting the present invention as the use of other dampening agents has been envisioned.

Injection port 89 can be positioned on annular undercut 85 and can be sealed by placing winged structure 15 on and covering injection port 89, thereby constraining the dampening agent to that portion of spring 9 near injection port 89. Alternatively, it is understood that a dampening agent can be located at surfaces in slidable engagement between needle hub 27 and front and rear barrels 11 and 13. This would produce a viscous shearing boundary layer that also can alter the velocity and acceleration of needle hub 27 retraction.

With reference to FIGS. 10-14, and with continuing reference to FIG. 9, fluid collection/infusion set 1 is used by folding panels 37 and 39 of winged structure 15 toward one another and into face-to-face engagement so that projections 45 on upper surface of panel 37 are received in recesses 47 on the upper surface of panel 39 to prevent shifting of panels 37 and 39. The tactile bumps (not shown) on the bottom surfaces of panels 37 and 39 can then be held securely in face-to-face engagement between a thumb and forefinger. Needle protector 29 is then separated from needle hub 27 to expose needle cannula 25. In this condition, the plane defined by abutting surfaces of panels 37 and 39 of winged structure 15 will lie on the plane of symmetry of puncture tip 35 of needle cannula 25.

Furthermore, front portion 49 of pivoting skin sensor lever 16 is in a downward position that is lower than needle cannula 25. Pivoting skin sensor lever 16 is biased in this position by the engagement of first engagement member 55 with forward recess 69. The healthcare professional then guides puncture tip 35 of needle cannula 25 into a targeted location on the patient and employs proximal fitting 5 at proximal end 17 of tubing 3 for connection to an evacuated container or a source of fluid that will be infused into the patient. The slotted arrangement on front portion 49 of pivoting skin sensor lever 16 straddles needle cannula 25 and does not obscure needle cannula 25 or the injection site. Furthermore, this slotted arrangement also acts as a guide to help in locating the ideal puncture site.

As the needle cannula 25 is inserted into the patient, pivoting skin sensor lever 16 pivots, in that front portion 49 of lever 16 is forced to move upward to at least the level of needle cannula 25, which in turn moves first engagement member 55 into an upward position based on the location of pivot axis 53. The upward movement of front portion 49 of pivoting skin sensor lever 16 causes first engagement member 55 to disengage from forward recess 69, thereby releasing the interference engagement between needle hub 27 and lever 16. This release of interference engagement permits the spring to exert a biasing force between the corresponding surfaces of needle hub 27 and front barrel 11, permitting the needle assembly 2 to be propelled or driven toward a second position with the puncture tip 35 of needle cannula 25 encompassed within the barrel assembly of front barrel 11 and rear barrel 13. For example, the spring 9 exerts a force between needle hub 27 and front barrel 11 such that they are moved axially and/or telescopically with respect to each other. The biasing force exerted between needle hub 27 and front barrel 11 may be less than the frictional force between the needle cannula and the patient's skin at the point of venipuncture, thereby preventing the needle cannula from retracting out of the patient's skin. Alternatively, it is contemplated that a secondary interference engagement exists between the pivoting lever 16 and the needle hub 27 after initial pivoting of the pivoting lever upon contact with the patient's skin and/or during venipuncture.

Figure 13:
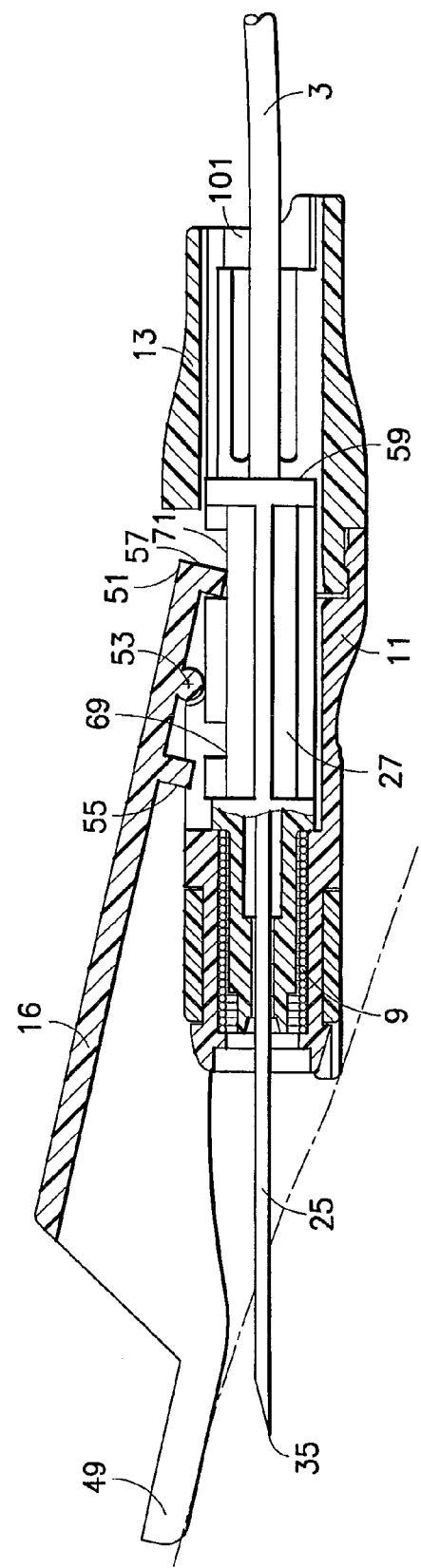
FIG. 13 is a side cross-sectional view of the needle assembly of FIG. 1 shown in use with a needle cannula piercing a patient's skin.

For example, such a secondary engagement may be provided through the interference engagement of second engagement member 57 at rear portion 51 of pivoting lever 16 with rearward recess 71 of needle hub 27 as shown in FIG. 13. Second engagement member 57 of pivoting lever 16 may be engaged with rearward recess 71 of needle hub 27 prior to the initial or upward pivotal movement of pivoting lever 16 about pivot axis 53, during contact and insertion or, more desirably, engages with rearward recess 71 during such initial or upward pivotal movement. In this manner, needle hub 27 is permitted to slide at least a minimal distance rearward based on the force exerted by spring 9 until being stopped by the engagement of second engagement member 57 with rearward recess 71, as shown in FIG. 13. Pivoting skin sensor lever 16 remains in this configuration for the duration of the injection or infusion.

Figure 15:
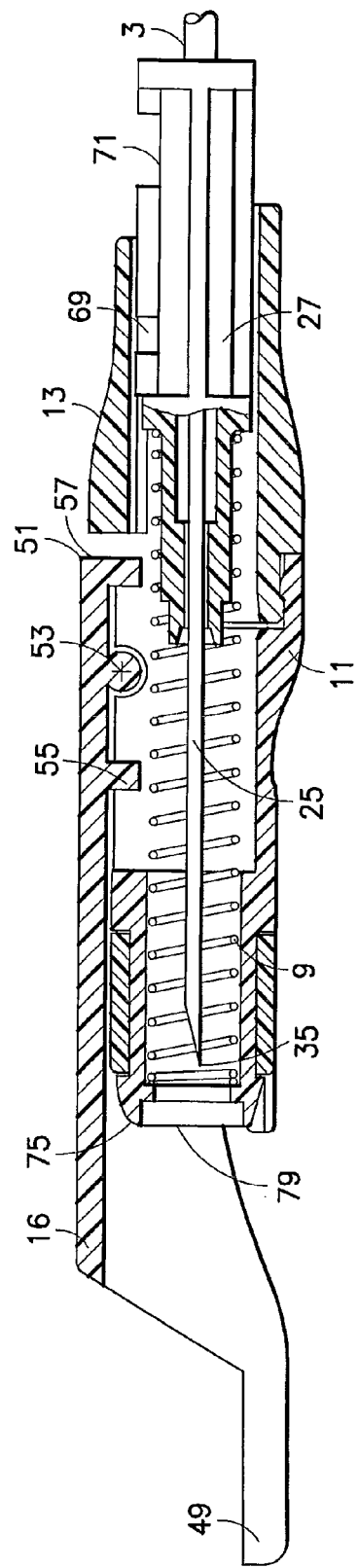
FIG. 15 is a side cross-sectional view of the needle assembly of FIG. 14.

Upon completion of the medical procedure, the healthcare professional removes needle cannula 25 from the patient. The removal of needle cannula 25 causes front portion 49 of pivoting skin sensor lever 16 to move downward toward its original position, causing pivoting lever 16 to pivot about pivot axis 53 in the opposite or reverse direction. This causes second engagement member 57 to be moved upward and out of rearward recess 71, while first engagement member 55 is simultaneously moved down to a position that does not engage forward recess 69. Hence, spring 9 is permitted to expand and propel needle portion 7 proximally. Proximal movement of needle portion 7 terminates when flange 67 abuts proximal flange 101 of rear barrel 13. In this position, the entirety of needle cannula 25 is disposed safely within front and/or rear barrels 11 and 13 as shown in FIG. 15.

As flange 67 of needle hub 27 approaches proximal flange 101, flange 67 also will engage locking fingers 103. Rearward movement of flange 67 causes an outward deflection of locking fingers 103. However, when flange 67 abuts proximal flange 101, locking fingers 103 resiliently return toward an undeflected condition and engage the distal face of flange 67. Hence, a return movement of needle portion 7 is prevented. Furthermore, the inwardly aligned orientation of locking fingers 103 substantially impedes any intentional outward deflection of locking fingers 103 that would permit a re-exposure of needle cannula 25. Hence, reuse of needle cannula 25 can be achieved only by a substantially complete destruction of locking fingers 103 in rear barrel 13.

Figure 16:
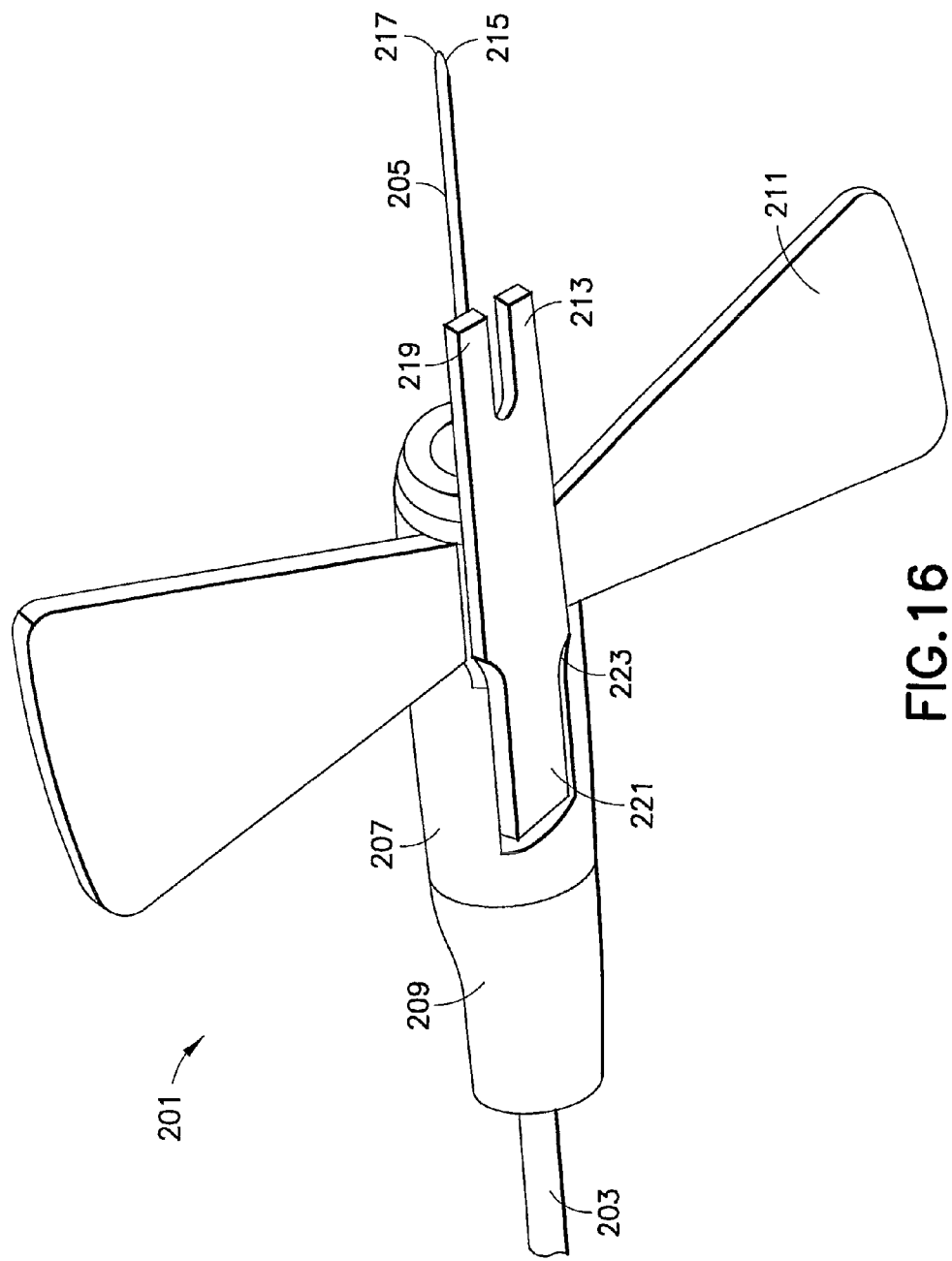
FIG. 16 is a perspective view of a needle assembly in accordance an alternate embodiment of the present invention.

With reference to FIG. 16, an alternate embodiment of the blood collection/infusion set 201 includes a length of flexible tubing 203, a needle assembly including a needle cannula 205, a spring (not shown), a barrel assembly that comprises a front barrel 207, a rear barrel 209, and a winged structure 211, and a pivoting skin sensor lever 213.

Needle cannula 205 has a proximal end supported by a needle hub positioned within front barrel 207, a distal end 215, and a lumen extending between the ends. Distal end 215 of needle cannula 205 is beveled to a sharp puncture tip 217, such as an intravenous puncture tip. Puncture tip 217 is provided for insertion into a patient's blood vessel, such as a vein, and is therefore designed to provide ease of insertion and minimal discomfort during venipuncture.

Pivoting skin sensor lever 213 includes a front portion 219 and a rear portion 221. Pivoting skin sensor lever 213 is attached to front barrel 207 with a pivot axis 223 substantially perpendicular to an axis of front barrel 207 and needle cannula 205. Pivot axis 223 is generally located on a lower surface of front barrel 207. Front portion 219 interfaces with the patient's point of injection by straddling needle cannula 205 and rear portion 221 interfaces with the needle hub (not shown). Front portion 219 of pivoting skin sensor 213 moves in an up and down manner, with the up direction being away from the patient's point of injection and the down direction being toward the point of injection. Front portion 219 of pivoting skin sensor lever 213 is configured to interface a patient's point of injection by straddling needle cannula 205, and may be further configured to include a slotted pad. The slotted pad offers more surface area and comfort to the patient. Front portion 219 of pivoting skin sensor lever 213 is further configured to be lower than needle cannula 205 when in a downward, initial position. Rear portion 221 also moves in an up and down manner, opposite to front portion 219 by virtue of the location of pivot axis 223. Pivot axis 223 may be formed by a pin and hole arrangement whereby pivoting skin sensor lever 213 is a separate component from front barrel 207. Pivot axis 223 may alternatively be molded integrally to front barrel 207. In this instance, pivot axis 223 may comprise two thin flexible members that create a hinge which is integral with front barrel 207.

The use of this embodiment is as follows. The healthcare professional first guides puncture tip 217 of needle cannula 205 into a targeted location on the patient and employs a proximal fitting (not shown) at a proximal end of tubing 203 for connection to an evacuated container or a source of fluid that will be infused into the patient. As the needle cannula 205 is inserted into the patient, front portion 219 of pivoting skin sensor lever 213 is forced to move upward to at least the level of needle cannula 205. The slotted arrangement on front portion 219 of pivoting skin sensor lever 213 straddles needle cannula 205 and does not obscure needle cannula 205 or the injection site. Furthermore, this slotted arrangement also acts as a guide to help in locating the ideal puncture site. The upward movement of front portion 219 of pivoting skin sensor lever 213 causes an engagement member (not shown) to disengage from a first recess in a needle hub (not shown) and allows a needle hub to slide a minimal distance rearward until being stopped by the engagement of another engagement member (not shown) with a second recess in the needle hub. Pivoting skin sensor lever 213 remains in this configuration for the duration of the injection or infusion. Upon completion of the medical procedure, the healthcare professional removes needle cannula 205 from the patient. The removal of needle cannula 205 causes front portion 219 of pivoting skin sensor lever 213 to move downward to its original position. This results in the other engagement member being moved upward and out of the second recess. Hence, a drive member (not shown) is permitted to expand and propels the needle hub proximally. Proximal movement of the needle hub terminates when the entirety of needle cannula 205 is disposed safely within front and rear barrels 207 and 209.

Figure 17:
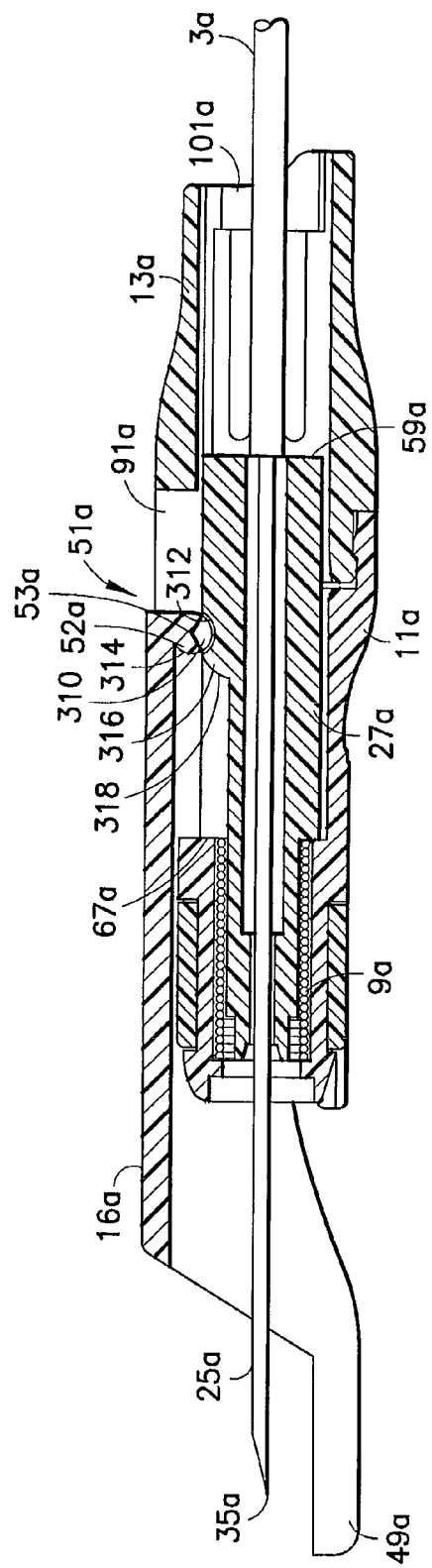
FIG. 17 is a side cross-sectional view in accordance with a further embodiment of the invention.
Figure 18:
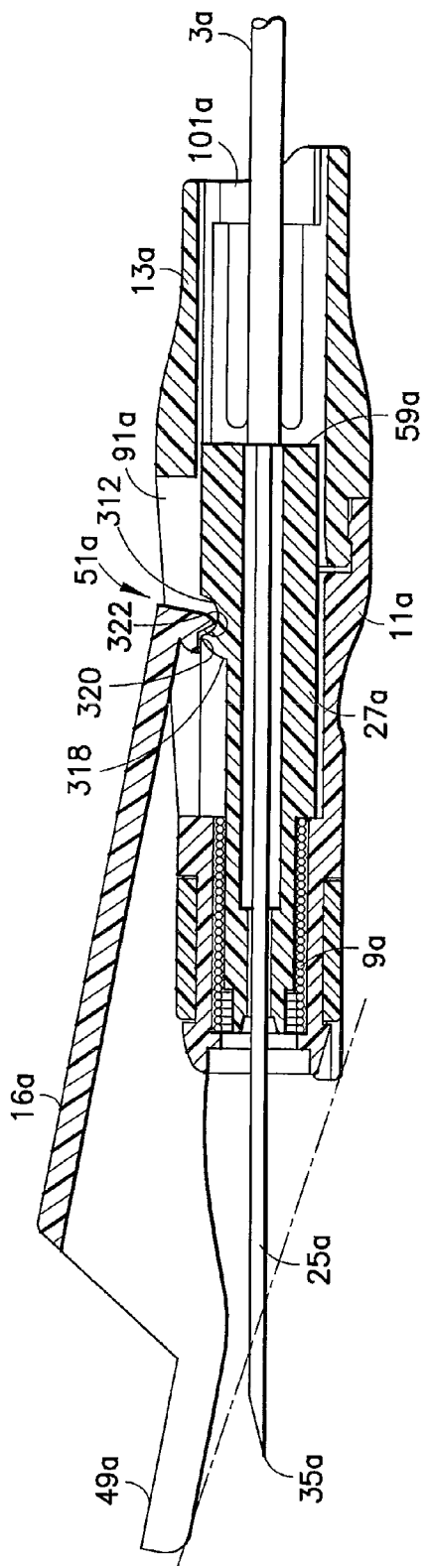
FIG. 18 is a side cross-sectional view of the needle assembly of FIG. 17 shown in use with a needle cannula piercing a patient's skin.
Figure 19:
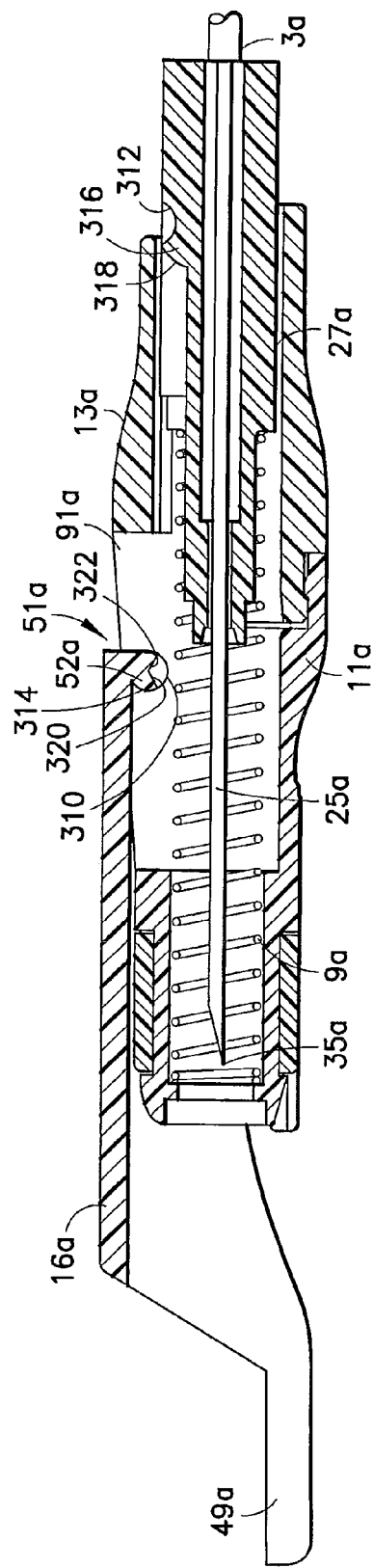
FIG. 19 is a side cross-sectional view of the needle assembly of FIG. 17 shown in a shielded position.

FIGS. 17-19 depict a further embodiment of the invention, incorporating an alternate retention and release mechanism between the lever and the hub. The embodiment depicted in FIGS. 17-19 includes similar components to those shown in FIGS. 12-15, and such similar components are identified with similar reference numbers and further including the designation "a". For example, the the blood collection/infusion set of FIGS. 17-19 includes a length of flexible tubing 3a, a needle assembly including a needle cannula 25a, a spring 9a, a barrel assembly that comprises a front barrel 11a, and a rear barrel 13a, and a pivoting skin sensor lever 16a.

Needle cannula 25a has a proximal end supported by a needle hub 27a positioned within the barrel assembly, a distal end defining an intravenous puncture tip 35a, and a lumen extending between the ends. Puncture tip 35a is provided for insertion into a patient's blood vessel, such as a vein, and is therefore designed to provide ease of insertion and minimal discomfort during venipuncture.

Pivoting skin sensor lever 16a includes a front portion 49a and a rear portion 51a. Front portion 49a interfaces with the patient's point of injection by straddling needle cannula 25a, while rear portion 51a interfaces with the needle hub 27a, as will be described in more detail herein. Pivoting skin sensor lever 16a is attached to front barrel 11a forming pivot axis 53a. Front barrel 11a further includes an opening 91a extending through the top wall surface thereof, dimensioned and configured to receive rear portion 51a of pivoting skin sensor 16a and permitting engagement of rear portion 51a with needle hub 27a.

As with the embodiment described in connection with FIGS. 12-15, pivot axis 53a may be formed through a lever bar arrangement, whereby the rear portion 51a of pivoting skin sensor lever 16a includes pin 52a connected to the front barrel 11a. For example, portions of the wall forming front barrel 11a may be cut away at opposing lateral sides thereof so as to accommodate pin 52a therein in a snap-fit engagement, providing for a hinge-like pivotal engagement about pivot axis 53a in a similar manner as described above in connection with FIGS. 12-15.

Rear portion 51a of lever 16a interfaces with needle hub 27a to maintain needle hub 27a against the bias of spring 9a. In particular, needle hub 27a may include a recess 312 extending through a portion of the top surface. Recess 312 is configured to accommodate pin 52a positioned at the rear portion 51a of lever 16a in a rotational manner, and therefore includes an internal surface which corresponds to the generally cylindrical external surface profile of pin 52a. Pin 52a is provided with a recessed portion extending between the lateral ends of pin 52a at a central cut-away portion 310. Central cut-away portion 310 may be in the form of a pie-shaped wedge cut out of the central portion of the general cylindrical cross-section of pin 52a, defining wedge faces 320, 322. Desirably, wedge faces 320, 322 intersect each other at an angle greater than 90° at the pivot axis 53a of pin 52a, forming central cut-away portion 310 as an obtuse angle. The external surface 314 of pin 52a, along with wedge faces 320, 322 at central cut-away portion 310, are designed to interact with the internal surface of recess 312 in order to retain needle hub 27a in a forward position against the force of spring 9a.

In particular, as shown in FIG. 17, an interference engagement is established between the external surface 314 of pin 52a and recess 312 of needle hub 27a, with external surface 314 acting as a first engagement portion, thereby maintaining needle hub 27a in place against the bias of spring 9a. As the needle cannula 25a is inserted into the patient, front portion 49a of pivoting skin sensor lever 16a is forced to move upward to at least the level of needle cannula 25a. The upward movement of front portion 49a of pivoting skin sensor lever 16a causes pin 52a to pivot about pivot axis 53a, as shown in FIG. 18. Such pivoting causes wedge face 320 to rotate out of interference engagement with shoulder 316 at the top surface of needle hub 27a. As such, pin 52a is essentially disengaged from a first position retaining needle hub 27a, and may even allow needle hub 27a to slide a minimal distance rearward, with wedge surface 322 contacting a lip portion at the forward edge of recess 312, thereby acting as a second engagement portion for further maintaining needle hub 27a against the bias of spring 9a. Pivoting skin sensor lever 16a remains in this configuration for the duration of the injection or infusion. Upon completion of the medical procedure, the healthcare professional removes needle cannula 25a from the patient. The removal of needle cannula 25a causes front portion 49a of pivoting skin sensor lever 16a to move downward to its original position, causing pin 52a to pivot about pivot axis 53a in a reverse direction. Such return pivoting causes wedge face 320 to ride about shoulder 316 and along shoulder face 318, which extends to a reduced profile channel surface extending along the top surface of needle hub 27a toward flange 67a. Such reverse or return pivoting movement causes wedge face 322 to pivot out of interference engagement with the lip portion at the forward edge of recess 312. In this manner, needle hub 27a is released from interference engagement, thereby permitting spring 9a to expand and propel the needle hub 27a proximally or rearwardly. Such proximal movement of needle hub terminates when the rearward or proximal end 59a of needle hub 27a contacts proximal flange 101a, with the entirety of needle cannula 25a disposed safely within front and rear barrels 11a and 13a as depicted in FIG. 19.

The shielding feature of the present invention is passively actuated upon normal usage of the device. In particular, upon contact with the skin of a patient and/or during venipuncture, the safety feature is primed and charged, ready for shielding the needle upon removal of the needle from the patient's skin. Accordingly, the user is not required to take any active steps to effect safety shielding of the needle, thereby automatically providing an effective safety feature through normal operation.

While the embodiments of the present invention have been described with reference to several figures of the passive retracting needle with skin sensor, those skilled in the art may make modifications and alterations. Accordingly, the above detailed description is intended to be illustrative rather than restrictive. Embodiments of the invention are defined by the appended claims, and all changes that fall within the meaning and range of equivalency of the claims are to be embraced within their scope.

The invention claimed is:

1. A safety needle device comprising:
   a hub including a passageway extending therethrough and a needle cannula having a puncture tip extending from a forward end thereof;
   a shield member in telescoping association with the hub, at least one of the hub and the shield member adapted for relative telescopic movement with respect to the other between a first position in which the puncture tip of the needle cannula is exposed from a forward end of the shield member and a second position in which the puncture tip of the needle cannula is encompassed within the shield member;
   a drive member disposed between the hub and the shield member and capable of biasing the hub and the shield member telescopically away from each other; and
   a contact member comprising a lever in pivotal engagement with the shield member including a forward portion adjacent the puncture tip of the needle cannula and a rearward portion including a structure to releasably maintain the hub and the shield member in the first position, the rearward portion of the lever being pivotally connected to the shield member, the contact member adapted to maintain the hub and the shield member in the first position against the bias of the drive member with the needle cannula exposed from the forward end of the shield member, and the contact member movable during contact with a surface, thereby permitting release of the hub and the shield member from the first position and permitting the drive member to bias at least one of the hub and the shield member toward the second position.

2. The safety needle device as in claim 1, wherein release of the contact member from the surface permits the drive member to bias at least one of the hub and the shield member telescopically away from each other to the second position with the puncture tip of the needle cannula encompassed within the shield member.

3. The safety needle device as in claim 1, wherein the rearward portion of the lever includes a first engagement portion for engaging with the hub to maintain the hub and the shield member in the first position, the first engagement member being releasable from engagement with the hub upon pivotal movement of the lever during contact with the surface.

4. The safety needle device as in claim 3, wherein the rearward portion of the lever further includes a second engagement portion for engaging with the hub upon pivotal movement of the lever during contact with the surface to maintain the hub from being biased entirely to the second position when the first engagement portion is released from engagement with the hub.

5. The safety needle device as in claim 4, wherein the second engagement portion is released from engagement with the hub upon pivotal movement of the lever in a reverse direction during release of contact with the surface.

6. The safety needle device as in claim 5, wherein the first engagement portion comprises a first engagement member and the second engagement portion comprises a second engagement member.

7. The safety needle device as in claim 5, wherein the lever includes a pivot pin for effecting pivotal movement of the lever about a pivot axis, and wherein the first engagement portion comprises a first external portion of the pivot pin, and wherein the second engagement portion comprises a second external portion of the pivot pin.

8. The safety needle device as in claim 7, wherein the pivot pin is substantially cylindrical including a wedge-shaped cut out portion, wherein the first external portion of the pivot pin comprises an external cylindrical surface of the pivot pin and wherein the second external portion comprises a face of the wedge-shaped cut out portion.

9. A shielding needle assembly comprising:
a needle cannula having a puncture tip at a distal end thereof;
a needle hub supporting the needle cannula;
a barrel having a proximal end, a distal end, and a passage extending between the ends, the needle hub being disposed in the passage of the barrel;
a drive member disposed between the barrel and the needle hub for driving the needle hub from a first position in which the puncture tip of the needle cannula is exposed from the distal end of the barrel to a second position where the puncture tip of the needle cannula is disposed entirely within the barrel; and
a lever pivotally connected to the barrel and including a forward portion adapted to contact a patient's skin surface and a rearward portion including a releasable engagement with the needle hub for maintaining the needle hub in the first position, the rearward portion of the lever being pivotally connected to the barrel,
wherein contact of the forward portion of the lever with the patient's skin surface pivots the lever and releases an initial engagement with the needle hub at the rearward portion of the lever.

10. The shielding needle assembly as in claim 9, wherein the rearward portion of the lever includes a first engagement portion engaging a portion of the needle hub, thereby maintaining the needle hub in the first position.

11. The shielding needle assembly of claim 10, wherein contact of the forward portion of the lever with the patient's skin surface, insertion of the needle cannula through the patient's skin surface, or contact of the forward portion of the lever with the patient's skin surface and insertion of the needle cannula through the patient's skin surface causes the lever to pivot with respect to the barrel such that the first engagement portion of the lever disengages from the needle hub.

12. The shielding needle assembly of claim 10, wherein the rearward portion of the lever further includes a second engagement portion for engagement with the needle hub, and wherein contact of the forward portion of the lever with the patient's skin surface, insertion of the needle cannula through the patient's skin surface, or contact of the forward portion of the lever with the patient's skin surface and insertion of the needle cannula through the patient's skin surface causes the lever to pivot with respect to the barrel such that the first engagement portion of the lever disengages from the needle hub and the second engagement portion of the lever maintains the needle hub in a position with the puncture tip extending from the forward end of the barrel.

13. The shielding needle assembly of claim 12, wherein the second engagement portion of the lever disengages from the needle hub upon pivotal movement of the lever with respect to the barrel in a reverse direction during removal of the forward portion of the lever from the patient's skin surface or during removal of the needle cannula from the patient's skin surface, thereby causing the drive member to drive the needle hub to a position wherein the puncture tip of the needle cannula is disposed entirely within the barrel.

14. The shielding needle assembly of claim 9, wherein the drive member comprises a coil spring.

15. The shielding needle assembly of claim 9, wherein the lever is integrally molded with the barrel.

16. The shielding needle assembly of claim 9, wherein the lever is pivotally connected to the barrel through a pivot pin.

17. The shielding needle assembly of claim 9, wherein the front portion of the pivoting lever is configured to interface a patient's point of injection by straddling the puncture tip of the needle cannula.

18. The shielding needle assembly of claim 17, wherein the front portion of the pivoting lever comprises a slotted pad.

19. A blood collection set comprising the shielding needle assembly of claim 9 including a flexible tubing extending from the needle hub, the flexible tubing comprising a non-patient needle cannula at an opposed end adapted for connection to a receptacle for accommodating a blood collection tube.

20. A method of actuating a needle assembly comprising:
providing a needle assembly comprising a hub including a needle cannula with a puncture tip extending from a forward end thereof, the hub at least partially disposed within a shield member and biased toward a position in which the puncture tip of the needle cannula is encompassed within the shield member, the needle assembly further comprising a pivotal lever connected to the shield member and including a first engagement with the hub for maintaining the hub against the bias with the puncture tip exposed from a forward end of the shield member;
inserting the puncture tip of the needle cannula through a skin surface of a patient such that the pivotal lever contacts the patient's skin surface and causes the lever to pivot with respect to the shield member, thereby releasing the first engagement between the lever and the hub; and removing the puncture tip of the needle cannula from the skin of the patient such that the pivotal lever releases from contact with the patient's skin surface and pivots with respect to the shield member in an opposite direction, thereby releasing the second engagement between the lever and the hub, and permitting the hub to be biased toward a position in which the puncture tip of the needle cannula is encompassed within the shield member.

* * * * *